(12) United States Patent
Nose

(10) Patent No.: US 9,927,532 B2
(45) Date of Patent: Mar. 27, 2018

(54) RADIATION DETECTION APPARATUS AND RADIATION TOMOGRAPHY APPARATUS

(71) Applicant: General Electric Company, Schenectady, NY (US)

(72) Inventor: Katsumasa Nose, Toyko (JP)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/312,567

(22) PCT Filed: May 19, 2015

(86) PCT No.: PCT/US2015/031457
§ 371 (c)(1),
(2) Date: Nov. 18, 2016

(87) PCT Pub. No.: WO2015/183625
PCT Pub. Date: Dec. 3, 2015

(65) Prior Publication Data
US 2017/0097423 A1 Apr. 6, 2017

(30) Foreign Application Priority Data
May 26, 2014 (JP) .................. 2014-107649

(51) Int. Cl.
*G01T 1/20* (2006.01)
*G01T 1/164* (2006.01)
*G21K 1/02* (2006.01)

(52) U.S. Cl.
CPC .......... *G01T 1/1648* (2013.01); *G01T 1/2018* (2013.01); *G21K 1/025* (2013.01)

(58) Field of Classification Search
CPC ........................... G01T 1/1648; G01T 1/2018
See application file for complete search history.

(56) References Cited

U.S. PATENT DOCUMENTS 4,039,836 A    8/1977   Shaw, IV
5,099,134 A *   3/1992   Hase ................. G21K 1/025
                                                       250/363.1

(Continued)

FOREIGN PATENT DOCUMENTS

JP    2001153960 A    6/2001
JP    2008168056 A    7/2008

(Continued)

OTHER PUBLICATIONS

JP Office Action for corresponding application No. 2014-107649, with English Translation of prior art, dated Apr. 18, 2017; 3 pages.

*Primary Examiner* — Kiho Kim

(57) ABSTRACT

A collimator, which is adhesively bonded to a detector element array, is prevented from falling off from the radiation detection apparatus even in case that a failure of the adhesive joint occurs in the collimator. There is provided a radiation detection apparatus comprising: a detector element array in which a plurality of detector elements are arranged substantially in a fan-angle direction and in a cone-angle direction of a radiation; a collimator adhesively bonded to a side of the detector element array on which the radiation impinges, and having outer end surfaces on both sides in the slice direction tapered to align with a direction of emission from a radiation source; and a pair of blocks disposed to sandwich the collimator in the cone-angle direction, and having inner end surfaces on both sides in the cone-angle direction tapered to align with the direction of emission.

20 Claims, 10 Drawing Sheets

(56) References Cited

U.S. PATENT DOCUMENTS

| | | | | |
|---|---|---|---|---|
| 5,991,357 | A | * 11/1999 | Marcovici | A61B 6/035 250/370.09 |
| 2012/0069954 | A1 | 3/2012 | Iso et al. | |
| 2012/0093280 | A1 | 4/2012 | Konno et al. | |
| 2012/0307963 | A1* | 12/2012 | Watanabe | A61B 6/4291 378/7 |
| 2013/0070892 | A1* | 3/2013 | Mori | A61B 6/032 378/7 |
| 2013/0134313 | A1* | 5/2013 | Niederlohner | G01T 1/16 250/363.03 |
| 2013/0235972 | A1* | 9/2013 | Kuroiwa | G21K 1/025 378/19 |

FOREIGN PATENT DOCUMENTS

| | | |
|---|---|---|
| JP | 2009282033 B2 | 12/2009 |
| JP | 2010223836 A | 10/2010 |
| JP | 2012086006 A | 5/2012 |
| JP | 2012137443 A | 7/2012 |
| WO | 2010150717 A1 | 12/2010 |

\* cited by examiner

FIG. 6
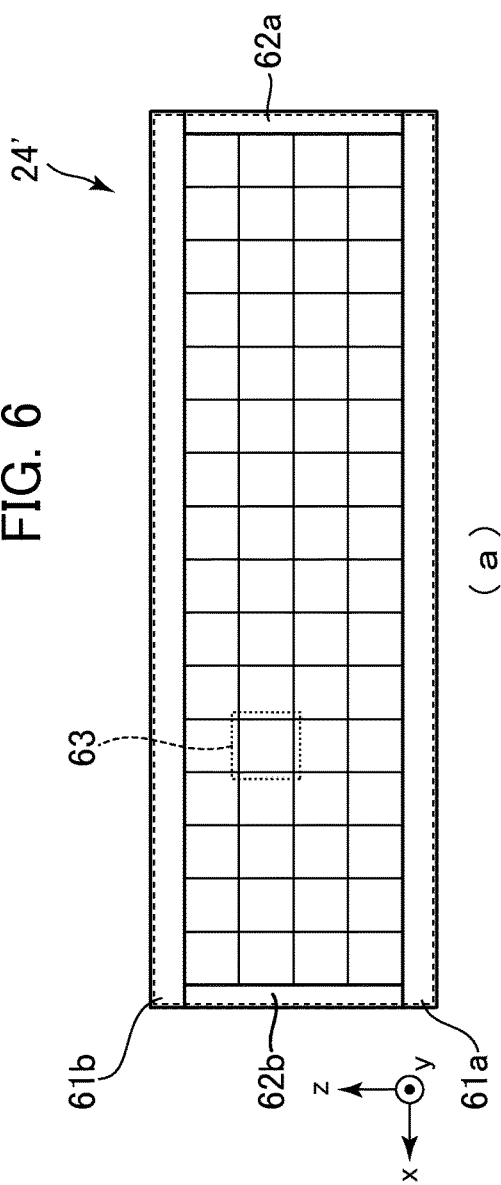
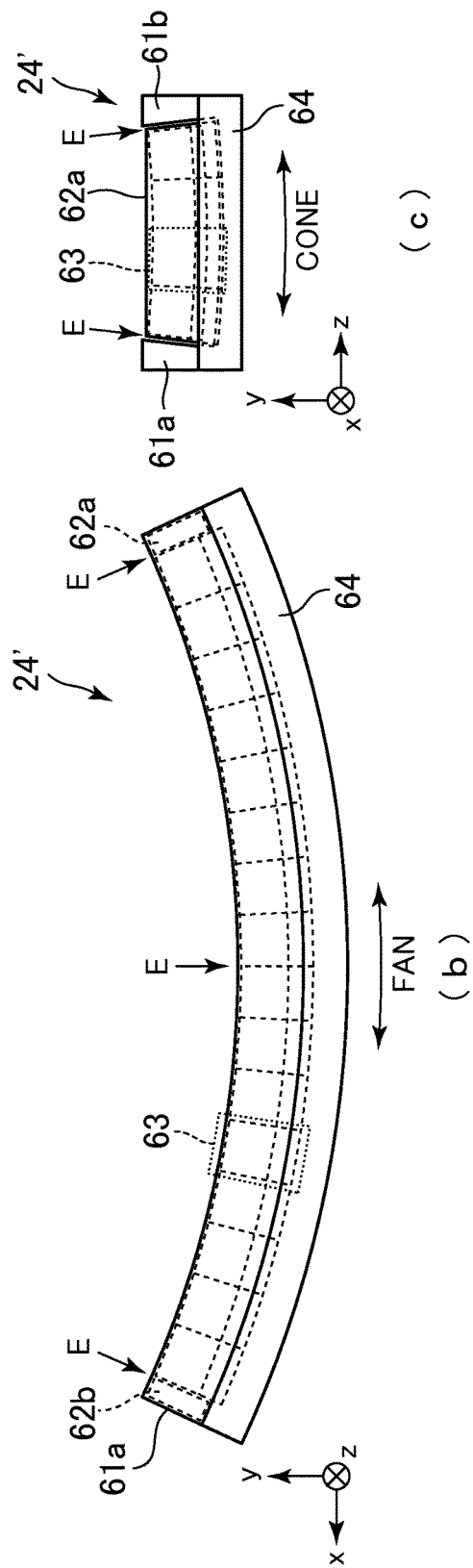

FIG. 7
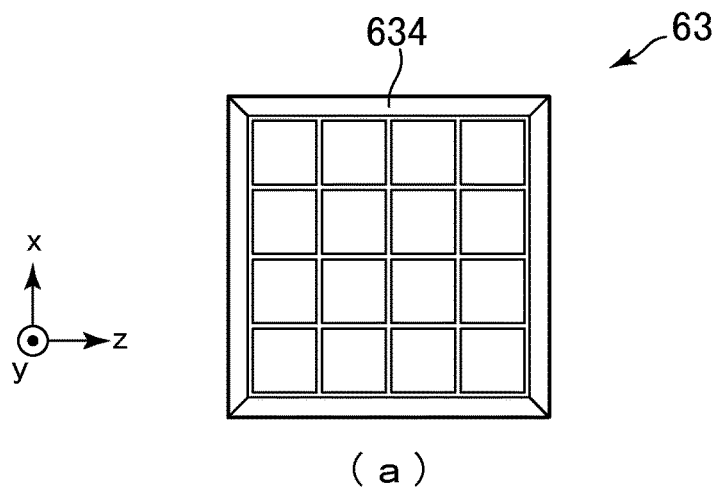
(a)
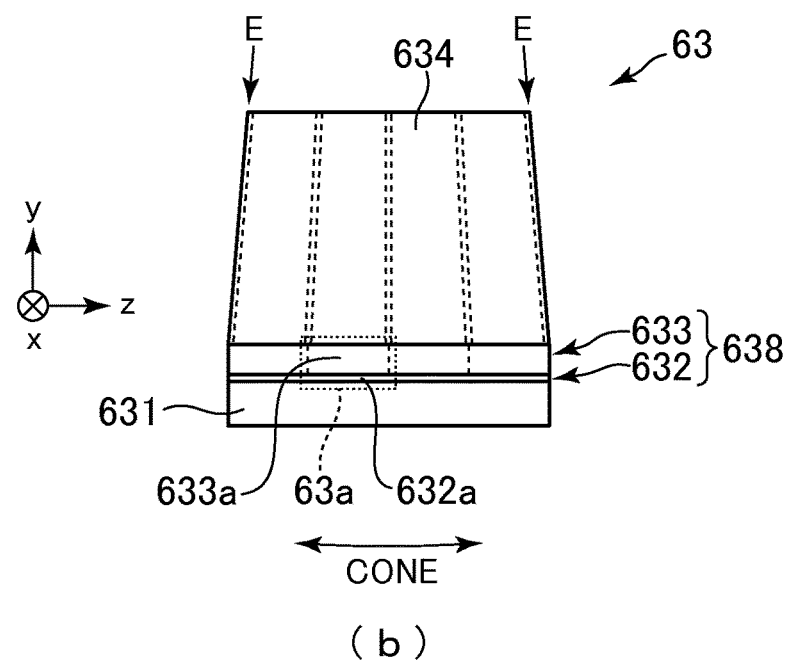
(b)

RADIATION DETECTION APPARATUS AND RADIATION TOMOGRAPHY APPARATUS

FIELD OF THE INVENTION

The present invention relates to a technique for a structure of a radiation detection apparatus used in a radiation tomography apparatus.

BACKGROUND

In a conventional radiation detection apparatus in a radiation tomography apparatus, a collimator and a detector element array are generally attached to each other as individual components (for example, see Abstract in Patent Document 1 and the like). However, since in recent years coverage in a slice direction is extended, and the collimator arcuately arranged facing a radiation source may lead to better control of image quality degradation, a construction having the collimator integrated with the detector element array is becoming mainstream. In such a construction, the collimator and detector element array are generally adhesively secured by an adhesive.

SUMMARY OF THE INVENTION

The collimator, however, is constructed of heavy metal such as tungsten, and therefore, it experiences a large centrifugal force by a rotation during a scan. Moreover, the collimator and detector elements have significantly different coefficients of linear expansion, so that their adhesive layer suffers from stress due to a change in ambient temperature. These phenomena may induce a failure in the adhesive layer with time, which causes the collimator to fall off.

In view of such circumstances, there is a need for a technique for preventing a collimator from falling off from a radiation detection apparatus even when a failure of the adhesive joint occurs in the collimator.

The invention in its first aspect provides a radiation detection apparatus for use in a radiation tomography apparatus, said radiation detection apparatus comprising:
a detector element array in which a plurality of detector elements are arranged substantially in a fan-angle direction and in a cone-angle direction of a radiation;
a collimator adhesively bonded to a side of said detector element array on which the radiation impinges, and having outer end surfaces on both sides in the cone-angle direction tapered to align with a direction of emission from a radiation source; and
a pair of blocks disposed to sandwich said collimator in the cone-angle direction, and having inner end surfaces on both sides in the cone-angle direction tapered to align with said direction of emission.

The invention in its second aspect provides the radiation detection apparatus in the aforementioned first aspect, wherein: said outer end surface in said collimator on either side lies close to said inner end surface in said pair of blocks on either side and separated by a space.

The invention in its third aspect provides the radiation detection apparatus in the aforementioned first aspect, wherein: said outer end surface in said collimator on either side is adjacent to said inner end surface in said pair of blocks on either side with an elastic material interposed therebetween.

The invention in its fourth aspect provides the radiation detection apparatus in any one of the aforementioned first through third aspects, wherein:
said collimator comprises a plurality of collimator modules arranged in the fan-angle direction, and
each of said plurality of collimator modules has both end surfaces in the cone-angle direction tapered to align with said direction of emission.

The invention in its fifth aspect provides the radiation detection apparatus in any one of the aforementioned first through fourth aspects, wherein:
said collimator comprises a plurality of collimator modules arranged in the cone-angle direction, and
each of said plurality of collimator modules has both end surfaces in the cone-angle direction tapered to align with said direction of emission.

The invention in its sixth aspect provides a radiation detection apparatus for use in a radiation tomography apparatus, said radiation detection apparatus comprising:
a detector element array in which a plurality of detector elements are arranged substantially in a fan-angle direction and in a cone-angle direction of a radiation;
a collimator adhesively bonded to a side of said detector element array on which the radiation impinges, and having outer end surfaces on both sides in the fan-angle direction tapered to align with a direction of emission from a radiation source; and
a pair of blocks disposed to sandwich said collimator in the fan-angle direction, and having inner end surfaces on both sides in the fan-angle direction tapered to align with said direction of emission.

The invention in its seventh aspect provides the radiation detection apparatus in the aforementioned sixth aspect, wherein: said outer end surface in said collimator on either side lies close to said inner end surface in said pair of blocks on either side and separated by a space.

The invention in its eighth aspect provides the radiation detection apparatus in the aforementioned sixth aspect, wherein: said outer end surface in said collimator on either side is adjacent to said inner end surface in said pair of blocks on either side with an elastic material interposed therebetween.

The invention in its ninth aspect provides the radiation detection apparatus in any one of the aforementioned sixth through eighth aspects, wherein:
said collimator comprises a plurality of collimator modules arranged in the fan-angle direction, and
each of said plurality of collimator modules has both end surfaces in the fan-angle direction tapered to align with said direction of emission.

The invention in its tenth aspect provides the radiation detection apparatus in any one of the aforementioned first through ninth aspects, wherein: said pair of blocks are included in a support portion for directly or indirectly supporting said detector element array.

The invention in its eleventh aspect provides a radiation tomography apparatus comprising the radiation detection apparatus in any one of the aforementioned first through tenth aspects.

According to the invention in the aspects described above, the radiation detection apparatus comprises a collimator having outer end surfaces on both sides in a specified direction tapered, the direction being a fan-angle direction or a cone-angle direction, and a pair of blocks disposed to sandwich the aforementioned collimator in the aforementioned specified direction, and having inner end surfaces on both sides in the aforementioned specified direction tapered; thus, even in case that adhesive delamination occurs between the collimator and detector element array, the collimator can be prevented from falling off to the outside of the aforementioned blocks by a what-is-called wedge effect.

BRIEF DESCRIPTION OF THE DRAWINGS

FIG. 6 is a diagram showing a configuration of an X-ray detector in accordance with a second embodiment;

FIG. 7 is a diagram showing a configuration of a second detector module;

DETAILED DESCRIPTION

Figure 1:
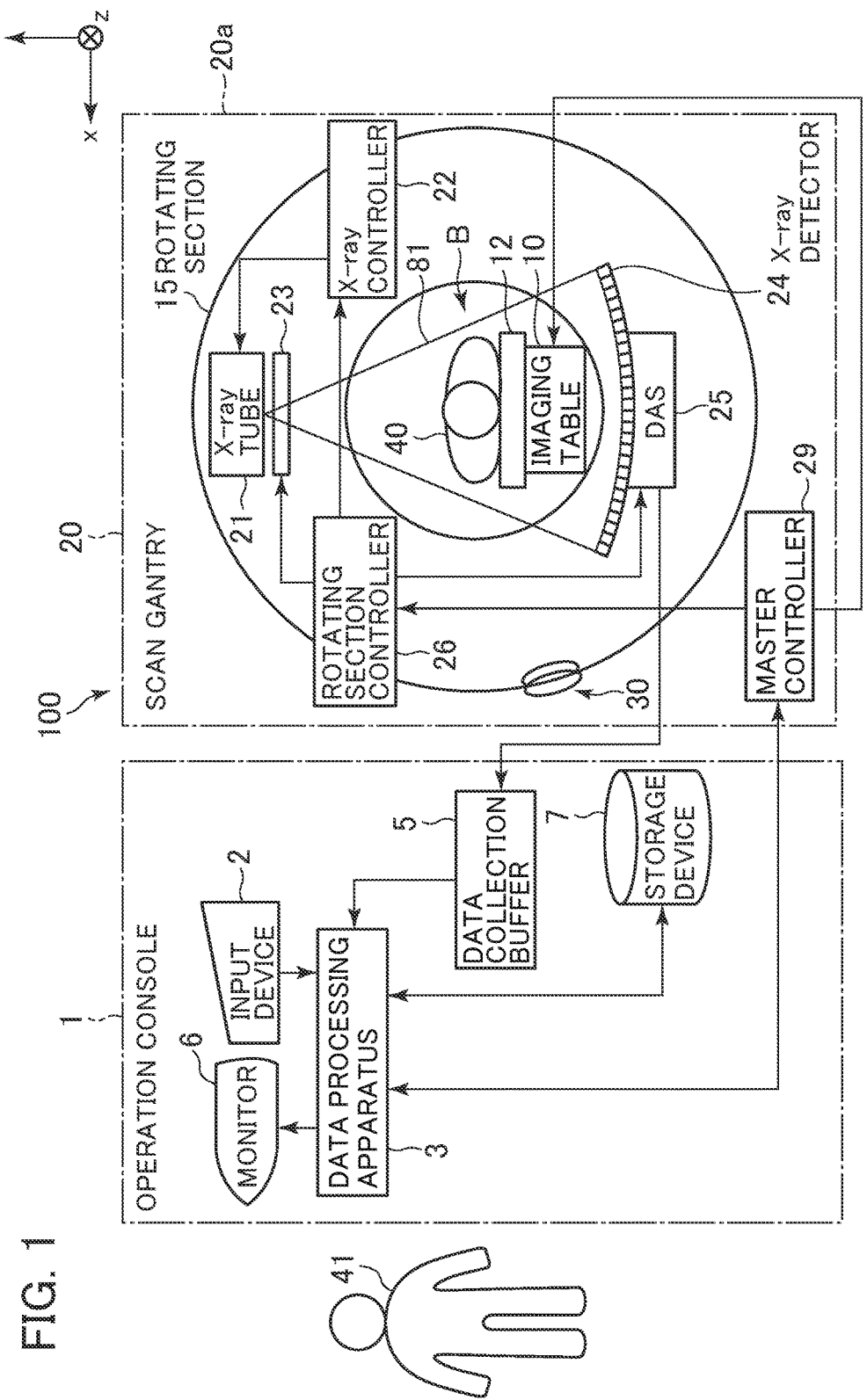
FIG. 1 is a diagram schematically showing a configuration of an X-ray CT apparatus in accordance with a first embodiment.

FIG. 1 is a diagram schematically showing a configuration of an X-ray CT (Computed Tomography) apparatus (radiation tomography apparatus) in accordance with a first embodiment.

As shown in FIG. 1, the X-ray CT apparatus 100 comprises an operation console 1, an imaging table 10, and a scan gantry 20.

The operation console 1 comprises an input device 2 for accepting an input from an operator 41, a data processing apparatus 3 for controlling several sections for imaging of a subject (object to be imaged) 40 and applying data processing for producing an image, etc., a data collection buffer 5 for collecting data acquired in the scan gantry 20, a monitor 6 for displaying an image, and a storage device 7 for storing therein programs, data, and the like.

The imaging table 10 comprises a cradle 12 for laying thereon the subject 40 to carry the subject 40 into a bore B in the scan gantry 20. The cradle 12 is vertically and horizontally translated by a motor incorporated in the imaging table 10. As used herein, a body axis direction of the subject 40, i.e., a direction of horizontal translation of the cradle 12, will be referred to as z-axis direction, a vertical direction as y-axis direction, and a horizontal direction perpendicular to the z- and y-axis directions as x-axis direction.

The scan gantry 20 comprises a rotatably supported rotating section 15. The rotating section 15 is provided with an X-ray tube 21, an X-ray controller 22 for controlling the X-ray tube 21, an aperture 23 for shaping X-rays 81 generated from the X-ray tube 21 into a fan beam or a cone beam, an X-ray detector (radiation detection apparatus) 24 for detecting the X-rays 81 passing through the subject 40, a DAS 25 for collecting output signals from the X-ray detector 24 as data, and a rotating section controller 26 for controlling the X-ray controller 22 and aperture 23. The body of the scan gantry 20 comprises a master controller 29 for communicating control signals and the like with the operation console 1 and imaging table 10. The rotating section 15 and the body of the scan gantry 20 are electrically connected to each other by a slip ring 30.

The X-ray tube 21 and X-ray detector 24 are placed facing each other on either side of an imaging volume in which the subject 40 is placed, i.e., the bore B of the scan gantry 20. A rotation of the rotating section 15 causes the X-ray tube 21 and X-ray detector 24 to rotate around the subject 40 while keeping their positional relationship. The X-rays 81 in the form of a fan or cone beam emitted from the X-ray tube 21 and shaped through the aperture 23 pass through the subject 40 and impinge upon a detecting surface of the X-ray detector 24.

As used herein, a body axis direction of the subject 40, i.e., a horizontal direction also defined as a direction of the axis of rotation of the rotating section 15, will be referred to as z-axis direction, a vertical direction as y-axis direction, and a horizontal direction orthogonal to the y- and z-axis directions as x-axis direction. Moreover, a direction of width of an arc of the X-rays 81 emitted in a fan shape from a focal spot f of the X-ray tube 21 will be referred to as fan-angle direction (FAN), a direction of the thickness of the arc of the X-rays 81 as cone-angle direction (CONE), and a direction of a straight line in which the X-rays 81 are emitted from the focal spot f of the X-ray tube 21 as direction of emission (E). The fan-angle direction and/or a tangential direction of the fan angle is also called channel direction (CH), and the z-axis direction and/or cone-angle direction is called slice direction (SL).

Figure 2:
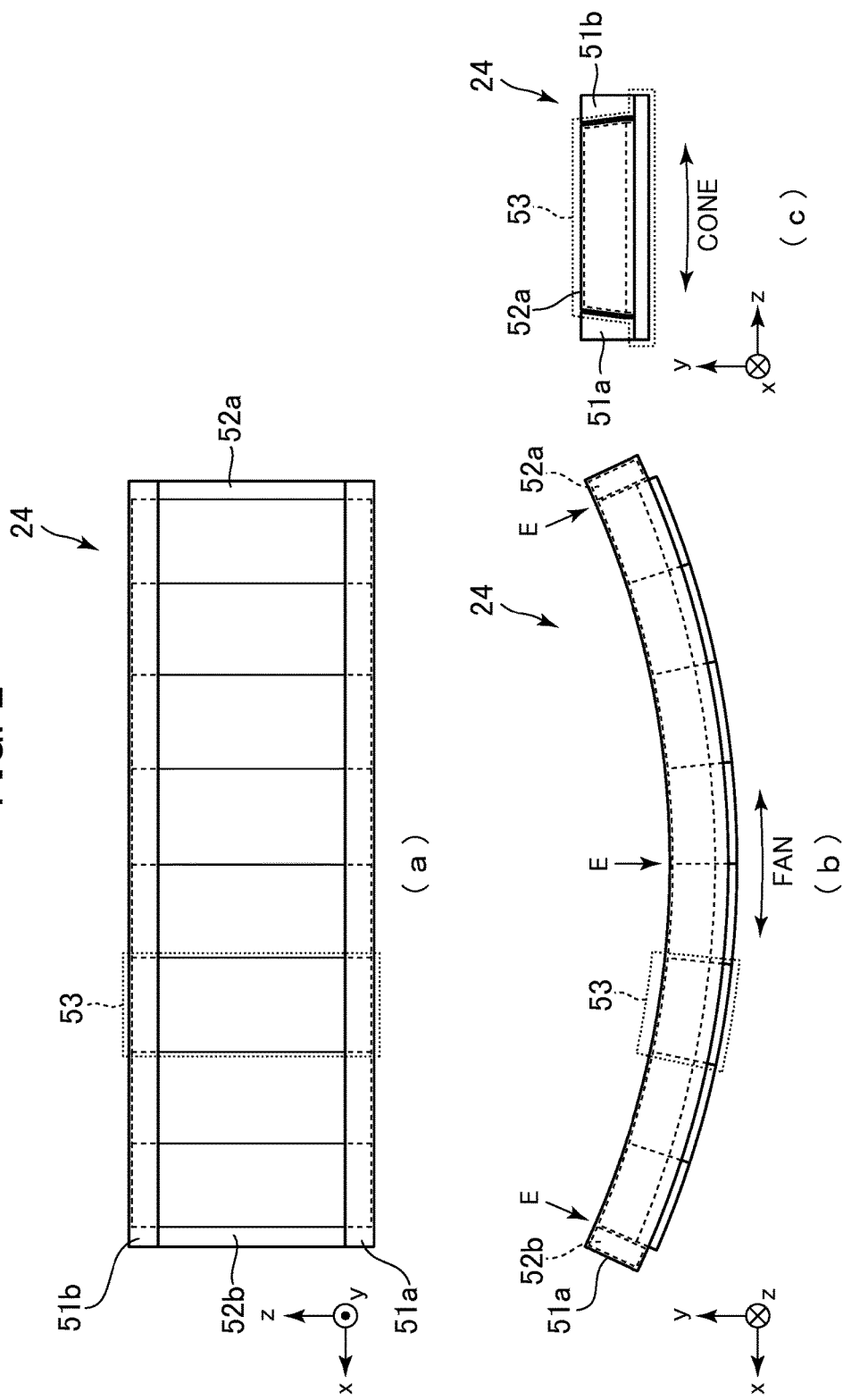
FIG. 2 is a diagram showing a configuration of an X-ray detector in accordance with the first embodiment.

FIG. 2 is a diagram showing a configuration of the X-ray detector 24 in accordance with the first embodiment.

The X-ray detector 24 is mainly comprised of a pair of rails (blocks) consisting of a first rail 51A and a second rail 51B, a pair of spacers consisting of a first spacer 52A and a second spacer 52B, and a plurality of first detector modules 53.

The first and second rails 51A, 51B have mutually similar shapes, and generally, are each arcuately curved in the fan-angle direction. The first rail 51A and second rail 51B are positioned in parallel with each other at a specific distance in the z-axis direction.

The first and second spacers 52A, 52B have mutually similar shapes, and generally, each have a columnar shape extending in the z-axis direction. The first spacer 52A and second spacer 52B are positioned in parallel with each other at a specific distance in the fan-angle direction (FAN). The first spacer 52A connects respective ends of the pair of rails 51A, 51B on one side in the fan-angle direction (FAN). The second spacer 52B connects respective ends of the pair of rails 51A, 51B on the other side in the fan-angle direction (FAN). The connection is achieved by, for example, screwing (not shown).

The plurality of first detector modules 53 each have a generally identical shape having its long-side direction in the z-axis direction. The plurality of first detector modules 53 are tightly arranged in the fan-angle direction (FAN). The plurality of first detector modules 53 each have one of its both ends in the z-axis direction attached to the first rail 51A and the other to the second rail 51B. This attachment is achieved by, for example, screwing (not shown). In practice, each of the plurality of first detector modules 53 is connected with a cable or circuitry for transmitting detected signals to the DAS 25, which is omitted in the drawing here.

Figure 3:
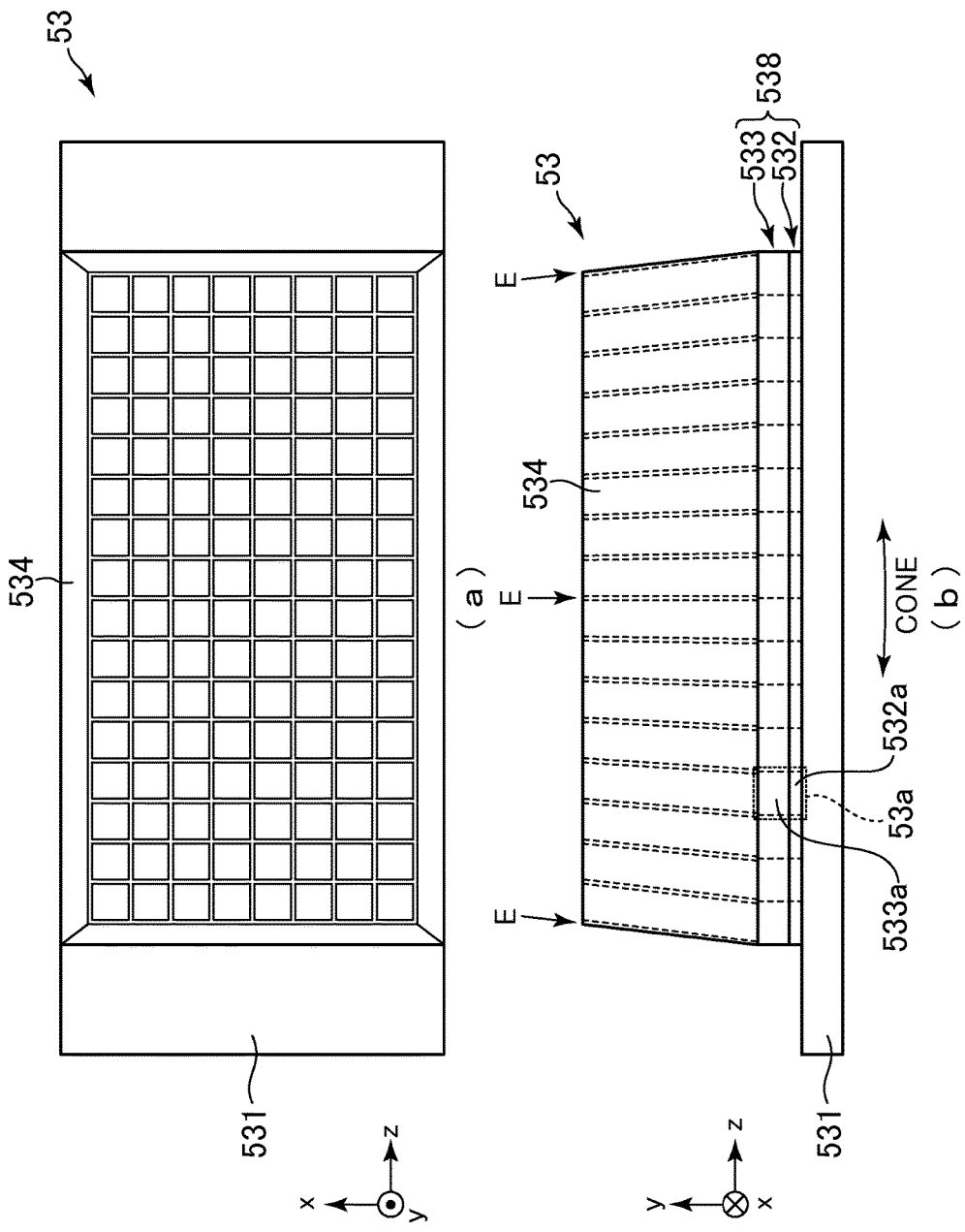
FIG. 3 is a diagram showing a configuration of a first detector module.

FIG. 3 is a diagram showing a configuration of a first detector module 53.

The first detector module 53 is mainly comprised of a substrate 531, a photodiode array 532, a scintillator array 533, and a collimator module 534.

The substrate 531 is a plate-like rectangle having its plate thickness direction in the direction of emission (E) and its long-side direction in the z-axis direction. The substrate 531 is constructed of ceramic, for example.

The substrate 531 has the photodiode array 532 formed on its plate surface on a side on which X-rays impinge, and the scintillator array 533 is laid over the photodiode array 532. The photodiode array 532 has a plurality of photodiode elements 532A in the form of a matrix in the channel direction (CH) and slice direction (SL). The scintillator array 533 has a plurality of scintillator elements 533A in the form of a matrix in the channel direction (CH) and slice direction (SL). The scintillator elements 533A and photodiode elements 532A correspond to one another in position in the direction of emission (E). Specifically, a single scintillator element 533A and a single photodiode element 532A corresponding to each other form a single detector element 53A, and the scintillator array 533 and photodiode array 532 form a detector element array 538. The number of detector elements per single detector module is 32 (CH)×64 (SL), for example, and the size of a single detector element is of the order of 1 mm square, for example. In the drawings to be referred to, a number of the detector elements, which is less than the actual number of the detector elements, are drawn for aiding understanding of the structure.

The detector element array 538 has the collimator module 534 adhesively secured on its surface on a side on which X-rays impinge, i.e., over the scintillator array 533, by an adhesive (not shown). The collimator module 534 is constructed of heavy metal such as, for example, tungsten or molybdenum. Moreover, the collimator module 534 is fabricated by a technique called DMLM (Direct Material Laser Melting), for example, which involves depositing layers of powder of such heavy metal melted using laser to form a desired shape.

The collimator module 534 is formed with grid-like walls that two-dimensionally separate individual detector elements 53A in the channel direction (CH) and slice direction (SL). Surfaces of the grid-like walls are each formed to align with the direction of emission (E). Thus, the collimator module 534 has outer end surfaces on both sides in the fan-angle direction (FAN) and those in the cone-angle direction (CONE) tapered to align with the direction of emission.

Figure 4:
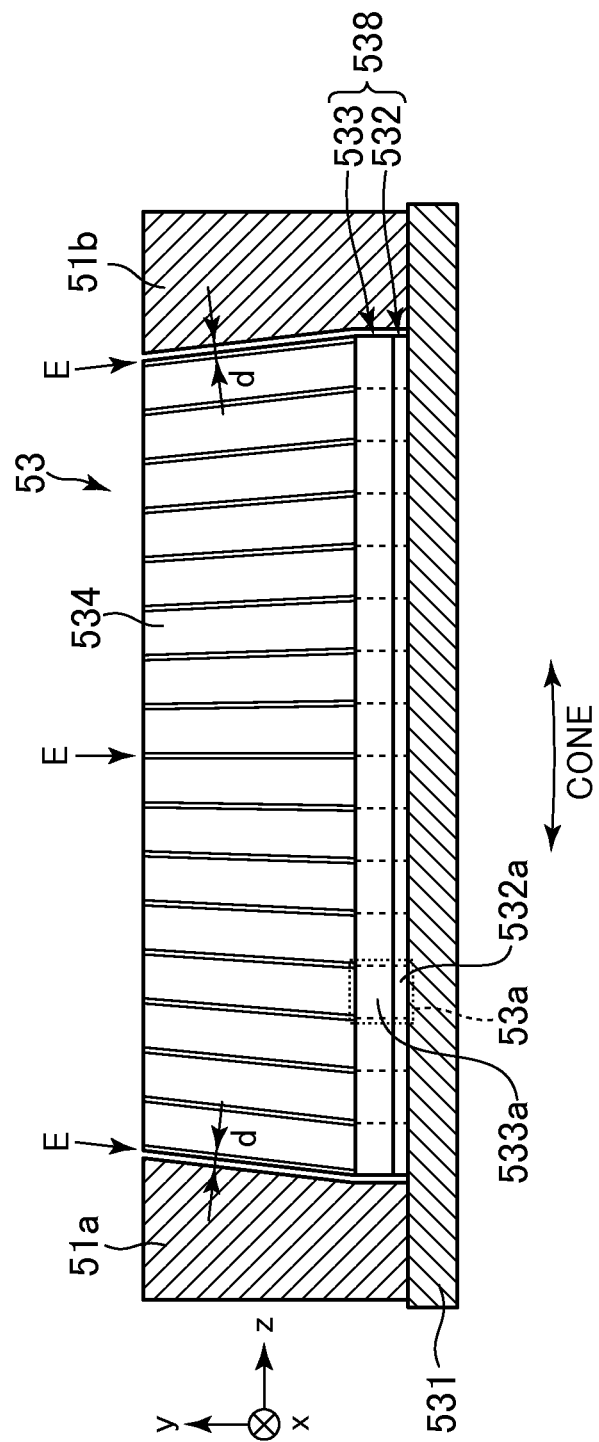
FIG. 4 is a vertical cross-sectional view representing a cross section perpendicular to the fan-angle direction of the X-ray detector in accordance with the first embodiment.

FIG. 4 is a vertical cross-sectional view representing a cross section perpendicular to the fan-angle direction (FAN) of the X-ray detector 24 in accordance with the first embodiment.

The detector modules 53 are each secured to the pair of rails 51A, 51B by screwing both ends of its substrate 531 in the z-axis direction thereto.

The pair of rails 51A, 51B are disposed to sandwich the collimator module 534 in each individual detector module 53 in the cone-angle direction (CONE). Inner end surfaces of the pair of rails 51A, 51B on both sides in the z-axis direction are tapered to align with the direction of emission (E). By such a configuration, a what-is-called wedge effect is produced between the collimator module 534 and pair of rails 51A, 51B. Accordingly, even when adhesion between the collimator module 534 and detector element array 538 is broken to cause the collimator module 534 to be delaminated from the detector element array 538, the collimator module 534 is prevented from falling off to the outside of the pair of rails 51A, 51B.

The inner end surface in the pair of rails 51A, 51B on either side and the outer end surface in the collimator module 534 on either side lie close to each other separated by a small gap d. The gap d has a size of the order of 10 µm-30 µm, for example. By such a configuration, even when the collimator module 534 and/or pair of rails 51A, 51B thermally expand, the outer end surface in the collimator module 534 on either side is prevented from coming into contact with the inner end surface in the pair of rails 51A, 51B on either side, thus preventing stress in the collimator module 534.

Figure 5:
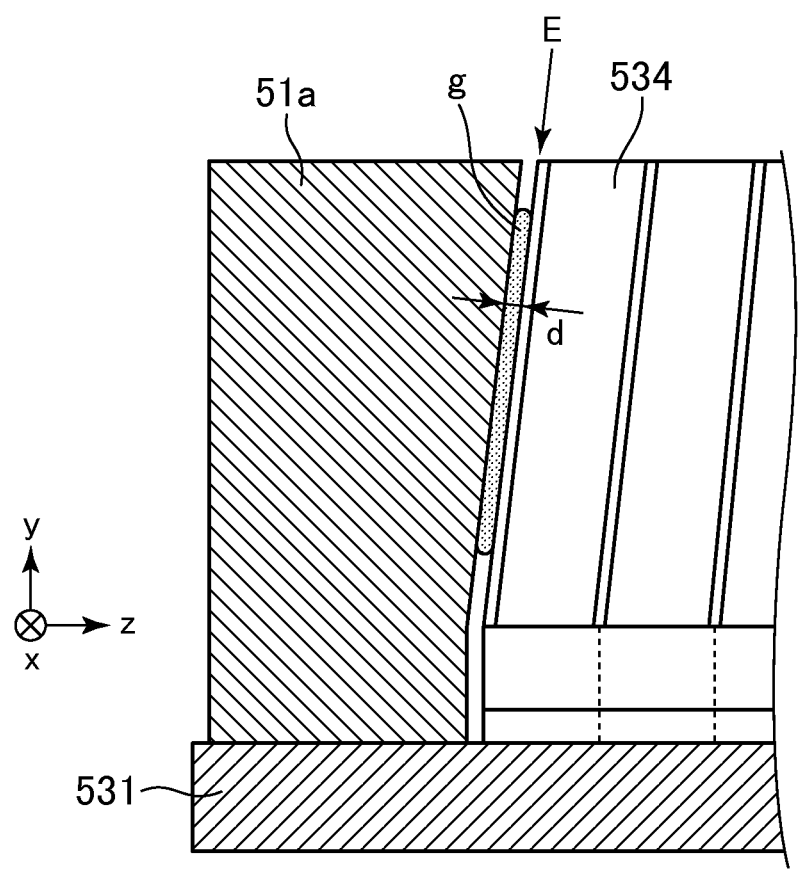
FIG. 5 is a partial enlarged view of a vertical cross section of the X-ray detector in accordance with the first embodiment.

FIG. 5 is a partial enlarged view of a vertical cross section of the X-ray detector 24 in accordance with the first embodiment. An elastic material g such as rubber or sponge may be interposed between the inner end surface in the pair of rails 51A, 51B on either side and the outer end surface in the collimator module 534 on either side, as shown in FIG. 5. By such a configuration, even when the collimator module 534 comes off, it is prevented from bumping in the inside of the pair of rails 51A, 51B, which promotes safety.

In this embodiment, the component disposed to sandwich the collimator module 534 in the cone-angle direction (CONE) forms part of the pair of rails 51A, 51B to which the detector module 53 is attached. Accordingly, this component does not need to be provided separately, which makes design and assembly easy and allows low-cost implementation.

Second Embodiment a. FIG. 6 is a diagram showing a configuration of an X-ray detector 24' in accordance with a second embodiment.

The X-ray detector 24' is mainly comprised of a pair of rails (blocks) consisting of a third rail 61A and a fourth rail 61B, a pair of spacers (blocks) consisting of a third spacer 62A and a fourth spacer 62B, a plurality of detector modules 63, and a base 64.

The third and fourth rails 61A, 61B have mutually similar shapes, and generally, are each arcuately curved in the fan-angle direction (FAN). The third rail 61A and forth rail 61B are positioned in parallel with each other at a specific distance in the z-axis direction.

The third and fourth spacers 62A, 62B have mutually similar shapes, and generally, each have a columnar shape extending in the z-axis direction. The third spacer 62A and fourth spacer 62B are positioned in parallel with each other at a specific distance in the fan-angle direction (FAN). The third spacer 62A connects respective ends of the pair of rails 61A, 61B on one side in the fan-angle direction (FAN). The forth spacer 62B connects respective ends of the pair of rails 61A, 61B on the other side in the fan-angle direction (FAN).

The base 64 is a component having a surface arcuately curved in the fan-angle direction (FAN) and cone-angle direction (CONE), and has a generally rectangular shape having its long-side direction in the fan-angle direction (FAN) as viewed from the focal spot f of the X-ray tube 21. The base 64 is provided with a plurality of second detector modules 63 placed on its curved surface on a side on which X-rays impinge, and the second detector modules 63 are arranged in the fan-angle direction (FAN) and cone-angle direction (CONE). With the plurality of second detector modules 63 placed thereon, the base 64 is connected to the pair of rails 61A, 61B and pair of spacers 62A, 62B from a side on which X-rays exit.

The plurality of second detector modules 63 each have a generally identical shape symmetric with respect to the fan-angle direction (FAN) and cone-angle direction (CONE). The plurality of second detector modules 63 are tightly arranged in the fan-angle direction (FAN) and cone-angle direction (CONE) in a region surrounded by the pair of rails 61A, 61B and pair of spacers 62A, 62B.

FIG. 7 is a diagram showing a configuration of a second detector module 63.

The second detector module 63 is mainly comprised of a substrate 631, a photodiode array 632, a scintillator array 633, and a collimator module 634.

The substrate 631 is a plate-like rectangle having its plate thickness direction in the direction of emission (E), and has a square plate surface having its equal sides in the channel direction (CH) and slice direction (SL). The substrate 631 is constructed of ceramic, for example.

The substrate 631 has the photodiode array 632 formed on its plate surface on a side on which X-rays impinge, and the scintillator array 633 is laid over the photodiode array 632. The photodiode array 632 has a plurality of photodiode elements 632a in the form of a matrix in the channel direction (CH) and slice direction (SL). The scintillator array 633 has a plurality of scintillator elements 633a in the form of a matrix in the channel direction (CH) and slice direction (SL). The scintillator elements 633a and photodiode elements (632A) correspond to one another in position in the direction of emission (E). Specifically, a single scintillator element 633A and a single photodiode element (632A) corresponding to each other form a single detector element 63A, and the scintillator array 633 and photodiode array 632 form a detector element array 638. The number of detector elements per single detector module is 16 (CH)×16 (SL), for example, and the size of a single detector element is of the order of 1 mm square, for example. In the drawings to be referred to, a number of the detector elements, which is less than the actual number of the detector elements, are drawn for aiding understanding of the structure.

The detector element array 638 has the collimator module 634 adhesively secured on its surface on a side on which X-rays impinge, i.e., over the scintillator array 633, by an adhesive (not shown). The collimator module 634 is constructed of heavy metal such as, for example, tungsten or molybdenum.

The collimator module 634 is formed with grid-like walls that two-dimensionally separate individual detector elements 63A in the channel direction (CH) and slice direction (SL). Surfaces of the grid-like walls are each formed to align with the direction of emission (E). Thus, the collimator module 634 has outer end surfaces on both sides in the fan-angle direction (FAN) and those in the cone-angle direction (CONE) tapered to align with the direction of emission.

Figure 8:
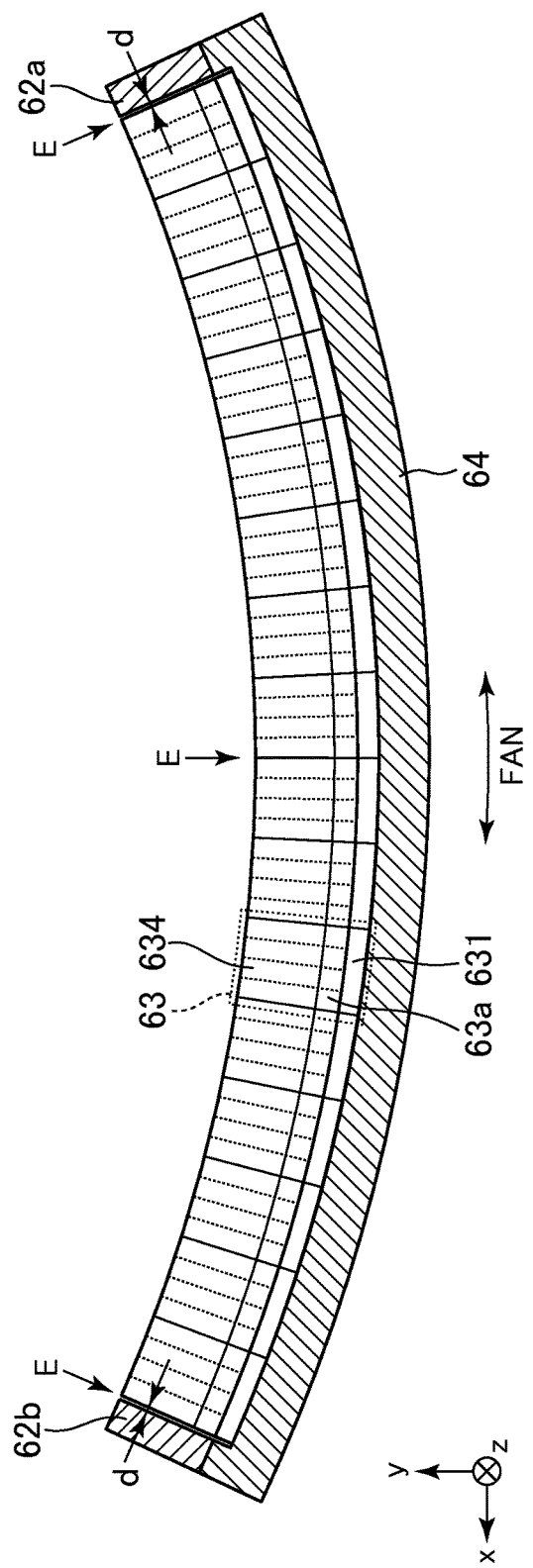
FIG. 8 is a vertical cross-sectional view representing a cross section perpendicular to the cone-angle direction of the X-ray detector in accordance with the second embodiment.
Figure 9:
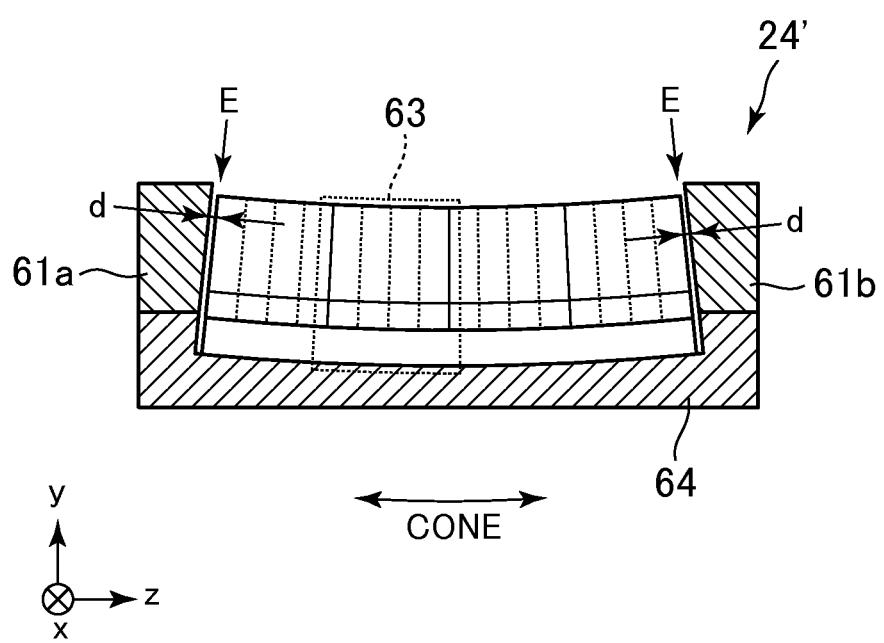
FIG. 9 is a vertical cross-sectional view representing a cross section perpendicular to the fan-angle direction of the X-ray detector in accordance with the second embodiment.

FIG. 8 is a vertical cross-sectional view representing a cross section perpendicular to the cone-angle direction (CONE) of the X-ray detector 24' in accordance with the second embodiment. FIG. 9 is a vertical cross-sectional view representing a cross section perpendicular to the fan-angle direction (FAN) of the X-ray detector 24' in accordance with the second embodiment.

The individual second detector modules 63 have their substrate 631 adhesively secured to a side of the base 64 on which X-rays impinge.

The pair of rails 61A, 61B are disposed to sandwich the collimator modules 634 in the cone-angle direction (CONE) in the second detector modules 63 arranged in the cone-angle direction (CONE). Inner end surfaces in the pair of rails 61A, 61B on both sides in the cone-angle direction (CONE) are tapered to align with the direction of emission (E). Moreover, the pair of spacers 62A, 62B are disposed to sandwich the collimator modules 634 in the fan-angle direction (FAN) in the second detector modules 63 arranged in the fan-angle direction (FAN). Inner end surfaces in the pair of spacers 62A, 62B on both sides in the fan-angle direction (FAN) are tapered to align with the direction of emission (E).

By such a configuration, a what-is-called wedge effect is produced between the plurality of collimator modules 634 arranged in the cone-angle direction (CONE) and the pair of rails 61A, 61B. The wedge effect is also produced between the plurality of collimator modules 634 arranged in the fan-angle direction (FAN) and the pair of spacers 62A, 62B. Accordingly, even when adhesion between the collimator module 634 and detector element array 638 is broken to cause the collimator module 634 to be delaminated from the detector element array 638, the collimator module 634 is prevented from falling off to the outside of the pair of rails 61A, 61B and pair of spacers 62A, 62B.

The inner end surface in the pair of rails 61A, 61B on either side in the cone-angle direction (CONE) and the outer end surface in the whole collimator modules 634 arranged in the cone-angle direction (CONE) on either side in the cone-angle direction (CONE) lie close to each other separated by a small gap d. Moreover, the inner end surface in the pair of spacers 62A, 62B on either side in the fan-angle direction (FAN) and the outer end surface in the whole collimator modules 634 arranged in the fan-angle direction (FAN) on either side in the fan-angle direction (FAN) also lie close to each other separated by a small gap d. These gaps d each have a size of the order of 10 μm-30 μm, for example. By such a configuration, even when the collimator module 634, pair of rails 61A, 61B and/or pair of spacers 62A, 62B thermally expand, the outer end surface in the collimator modules 634 on either side is prevented from coming into contact with the pair of rails 61A, 61B and/or pair of spacers 62A, 62B, thus preventing stress in the collimator modules 634.

Figure 10:
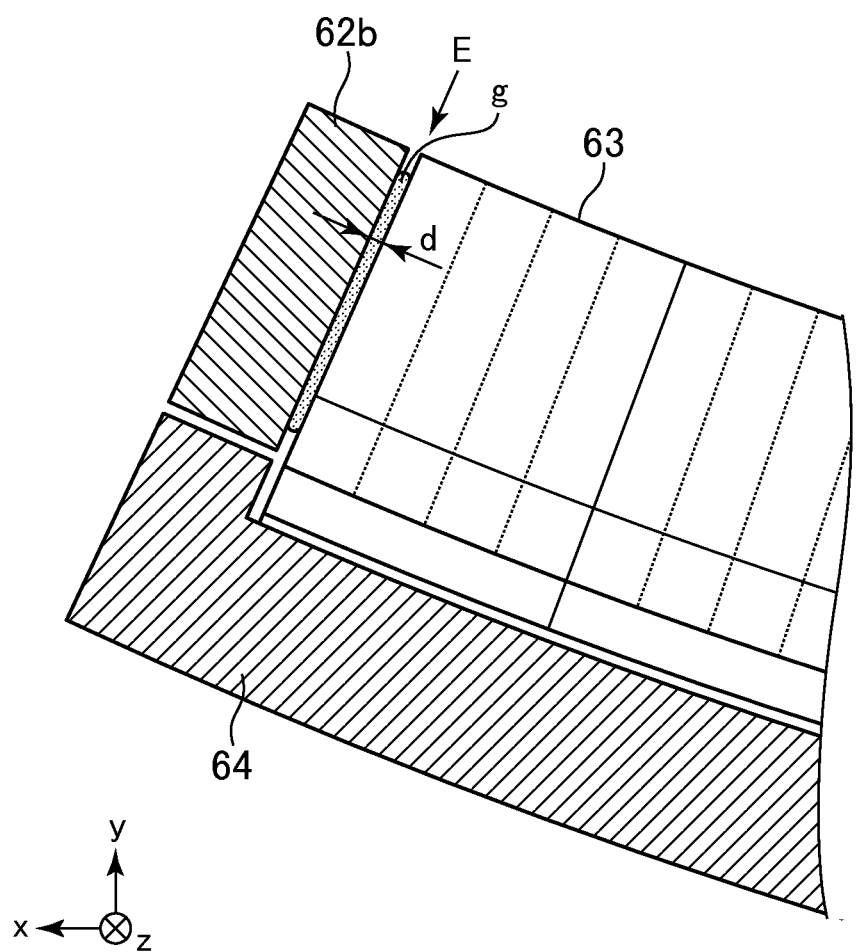
FIG. 10 is a partial enlarged view of a vertical cross-sectional view of the X-ray detector in accordance with the second embodiment.

FIG. 10 is a partial enlarged view of a vertical cross section of the X-ray detector 24' in accordance with the second embodiment. In the present embodiment, an elastic material g such as rubber or sponge may be interposed between the inner end surface in the pair of spacers 62A, 62B on either side in the fan-angle direction (FAN) and the outer end surface in the plurality of collimator modules 634 arranged in the fan-angle direction (FAN) on either side in the fan-angle direction (FAN), as shown in FIG. 10. Likewise, an elastic material g such as rubber or sponge may be interposed between the inner end surface in the pair of rails 61A, 61B on either side in the cone-angle direction (CONE) and the outer end surface in the plurality of collimator modules 634 arranged in the cone-angle direction (CONE) on either side in the cone-angle direction (CONE). By such a configuration, even when the collimator module 634 comes off, it is prevented from bumping in the inside of pair of rails 61A, 61B and pair of spacers 62A, 62B, which promotes safety.

Moreover, the second detector module 63 may have a configuration in which a plurality of collimator modules are combined with a single detector element array 638. By such a configuration, reduction of process steps in fabrication or assembly of the X-ray detector 24' and enhancement of accuracy may be possible.

According to the embodiments described above, the X-ray detector comprises a collimator having outer end surfaces on both sides in a specified direction tapered, the direction being a cone-angle direction (CONE) or a fan-angle direction (FAN), and a pair of blocks disposed to sandwich the aforementioned collimator in the aforementioned specified direction, and having inner end surfaces on both sides in the aforementioned specified direction tapered; thus, even in case that adhesive delamination occurs between the collimator and detector element array, the collimator can be prevented from falling off from the aforementioned X-ray detector by a what-is-called wedge effect.

The present invention is not limited to the embodiments described above and several modifications may be made without departing from the spirit and scope of the invention.

For example, while the embodiments described above refer to the X-ray CT apparatus, the present invention may be applied to a PET-CT or SPECT-CT apparatus in which an X-ray CT apparatus is combined with PET or SPECT.

What is claimed is:

1. A radiation detection apparatus for use in a radiation tomography apparatus, said radiation detection apparatus comprising:
    a detector element array in which a plurality of detector elements are arranged substantially in a fan-angle direction and in a cone-angle direction of a radiation;
    a collimator adhesively bonded to a side of said detector element array on which the radiation impinges, and having outer end surfaces on both sides in the cone-angle direction tapered to align with a direction of emission from a radiation source; and
    a pair of blocks disposed to sandwich said collimator in the cone-angle direction, and having inner end surfaces on both sides in the cone-angle direction tapered to align with said direction of emission.

2. The radiation detection apparatus as recited in claim 1, wherein: said outer end surface in said collimator on either side lies close to said inner end surface in said pair of blocks on either side and separated by a space.

3. The radiation detection apparatus as recited in claim 1, wherein: said outer end surface in said collimator on either side is adjacent to said inner end surface in said pair of blocks on either side with an elastic material interposed therebetween.

4. The radiation detection apparatus as recited in claim 1, wherein:
    said collimator comprises a plurality of collimator modules arranged in the fan-angle direction, and
    each of said plurality of collimator modules has both end surfaces in the cone-angle direction tapered to align with said direction of emission.

5. The radiation detection apparatus as recited in claim 1, wherein:
    said collimator comprises a plurality of collimator modules arranged in the cone-angle direction, and
    each of said plurality of collimator modules has both end surfaces in the cone-angle direction tapered to align with said direction of emission.

6. A radiation detection apparatus for use in a radiation tomography apparatus, said radiation detection apparatus comprising:
    a detector element array in which a plurality of detector elements are arranged substantially in a fan-angle direction and in a cone-angle direction of a radiation;
    a collimator adhesively bonded to a side of said detector element array on which the radiation impinges, and having outer end surfaces on both sides in the fan-angle direction tapered to align with a direction of emission from a radiation source; and
    a pair of blocks disposed to sandwich said collimator in the fan-angle direction, and having inner end surfaces on both sides in the fan-angle direction tapered to align with said direction of emission.

7. The radiation detection apparatus as recited in claim 6, wherein: said outer end surface in said collimator on either side lies close to said inner end surface in said pair of blocks on either side and separated by a space.

8. The radiation detection apparatus as recited in claim 6, wherein: said outer end surface in said collimator on either side is adjacent to said inner end surface in said pair of blocks on either side with an elastic material interposed therebetween.

9. The radiation detection apparatus as recited in any claim 6, wherein:
    said collimator comprises a plurality of collimator modules arranged in the fan-angle direction, and
    each of said plurality of collimator modules has both end surfaces in the fan-angle direction tapered to align with said direction of emission.

10. The radiation detection apparatus as recited in claim 6, wherein: said pair of blocks are included in a support portion for directly or indirectly supporting said detector element array.

11. A radiation tomography apparatus including a radiation detection apparatus, said radiation detection apparatus comprising:
    a detector element array in which a plurality of detector elements are arranged substantially in a fan-angle direction and in a cone-angle direction of a radiation;
    a collimator adhesively bonded to a side of said detector element array on which the radiation impinges, and having outer end surfaces on both sides in the cone-angle direction tapered to align with a direction of emission from a radiation source; and
    a pair of blocks disposed to sandwich said collimator in the cone-angle direction, and having inner end surfaces on both sides in the cone-angle direction tapered to align with said direction of emission.

12. The radiation tomography apparatus as recited in claim 11, wherein:
    said outer end surface in said collimator on either side lies close to said inner end surface in said pair of blocks on either side and separated by a space.

13. The radiation tomography apparatus as recited in claim 12, wherein:
    said collimator comprises a plurality of collimator modules arranged in the fan-angle direction, and
    each of said plurality of collimator modules has both end surfaces in the cone-angle direction tapered to align with said direction of emission.

14. The radiation tomography apparatus as recited in claim 12, wherein:
    said collimator comprises a plurality of collimator modules arranged in the cone-angle direction, and
    each of said plurality of collimator modules has both end surfaces in the cone-angle direction tapered to align with said direction of emission.

15. The radiation tomography apparatus as recited in claim 11, wherein:
    said outer end surface in said collimator on either side is adjacent to said inner end surface in said pair of blocks on either side with an elastic material interposed therebetween.

16. The radiation tomography apparatus as recited in claim 15, wherein:

said collimator comprises a plurality of collimator modules arranged in the fan-angle direction, and each of said plurality of collimator modules has both end surfaces in the cone-angle direction tapered to align with said direction of emission.

17. The radiation tomography apparatus as recited in claim 15, wherein:

said collimator comprises a plurality of collimator modules arranged in the cone-angle direction, and each of said plurality of collimator modules has both end surfaces in the cone-angle direction tapered to align with said direction of emission.

18. The radiation tomography apparatus as recited in claim 11, wherein:

said collimator comprises a plurality of collimator modules arranged in the fan-angle direction, and each of said plurality of collimator modules has both end surfaces in the cone-angle direction tapered to align with said direction of emission.

19. The radiation tomography apparatus as recited in claim 18, wherein:

said collimator comprises a plurality of collimator modules arranged in the cone-angle direction, and each of said plurality of collimator modules has both end surfaces in the cone-angle direction tapered to align with said direction of emission.

20. The radiation tomography apparatus as recited in claim 11, wherein:

said collimator comprises a plurality of collimator modules arranged in the cone-angle direction, and each of said plurality of collimator modules has both end surfaces in the cone-angle direction tapered to align with said direction of emission.

* * * * *